(12) United States Patent
Todd et al.

(10) Patent No.: US 9,320,646 B2
(45) Date of Patent: Apr. 26, 2016

(54) SYSTEM AND METHOD FOR A PROCEDURE BASED GRAPHICAL INTERFACE

(75) Inventors: Kirk W. Todd, Yorba Linda, CA (US);
Paul J. Essex, Rancho Santa Margarita, CA (US); Johan Ekvall, Laguna Beach, CA (US); Torsten A. Gelland, Irvine, CA (US); Roger D. Thomas, Tustin, CA (US)

(73) Assignee: Novartis AG, Basel (CH)

( * ) Notice: Subject to any disclaimer, the term of this patent is extended or adjusted under 35 U.S.C. 154(b) by 2112 days.

(21) Appl. No.: 11/679,016

(22) Filed: Feb. 26, 2007

(65) Prior Publication Data
US 2007/0202479 A1 Aug. 30, 2007

Related U.S. Application Data

(60) Provisional application No. 60/776,998, filed on Feb. 27, 2006.

(51) Int. Cl.
| | |
|---|---|
| *A61B 8/14* | (2006.01) |
| *A61F 9/007* | (2006.01) |
| *A61B 19/02* | (2006.01) |
| *G06F 19/00* | (2011.01) |
| *G09B 23/28* | (2006.01) |
| *A61B 17/00* | (2006.01) |

(52) U.S. Cl.
CPC .............. *A61F 9/007* (2013.01); *A61B 19/0248* (2013.01); *G06F 19/3406* (2013.01); *G09B 23/28* (2013.01); *A61B 2017/00199* (2013.01); *A61B 2019/025* (2013.01); *A61B 2019/0255* (2013.01)

(58) Field of Classification Search
USPC ........................ 606/1; 600/437; 715/771, 763
See application file for complete search history.

(56) References Cited

U.S. PATENT DOCUMENTS

| | | | |
|---|---|---|---|
| 4,395,258 A | 7/1983 | Wang et al. | |
| 4,493,695 A | 1/1985 | Cook | |

(Continued)

FOREIGN PATENT DOCUMENTS

| | | |
|---|---|---|
| EP | 1872736 A2 | 1/2008 |
| EP | 1872736 A3 | 4/2008 |

(Continued)

OTHER PUBLICATIONS

International Searching Authority, Written Opinion of the International Searching Authority, International Application No. PCT/US2008/067671, Apr. 6, 2009, 5 pages.

(Continued)

*Primary Examiner* — William Thomson
*Assistant Examiner* — Jeffrey Lipitz

(57) ABSTRACT

Embodiments of the present invention may allow each of the surgical steps of a surgical procedure to be defined and associated with a function of the surgical console using a GUI. The defined surgical procedure can then be saved and later invoked by a user of the surgical console to conduct the surgical procedure. When the saved surgical procedure is invoked representations of the defined surgical steps are displayed to the user using a GUI so the user can conduct the surgical procedure by navigating through the representations of the surgical steps such that when a representation of a surgical step is selected the surgical console is configured according to the functionality associated with that surgical step.

20 Claims, 10 Drawing Sheets

(56) References Cited

U.S. PATENT DOCUMENTS

| | | | |
|---|---|---|---|
| 4,627,833 | A | 12/1986 | Cook |
| 4,713,051 | A | 12/1987 | Steppe |
| 4,758,238 | A | 7/1988 | Sundblom |
| 4,790,816 | A | 12/1988 | Sundblom |
| 4,798,850 | A | 1/1989 | Brown |
| 5,455,766 | A | 10/1995 | Scheller et al. |
| 5,554,894 | A | 9/1996 | Sepielli |
| 5,997,528 | A | 12/1999 | Bisch et al. |
| 6,036,458 | A | 3/2000 | Cole |
| 6,041,259 | A | 3/2000 | Agarwala et al. |
| 6,059,544 | A | 5/2000 | Jung |
| 6,251,113 | B1 | 6/2001 | Appelbaum et al. |
| 6,267,956 | B1 | 7/2001 | Gomes |
| 6,292,178 | B1 * | 9/2001 | Bernstein et al. ............ 345/173 |
| 6,293,926 | B1 | 9/2001 | Sorensen |
| 6,364,342 | B1 | 4/2002 | Kim |
| 6,451,015 | B1 | 9/2002 | Rittman, III et al. |
| 6,602,227 | B1 | 8/2003 | Cimino et al. |
| 6,707,476 | B1 | 3/2004 | Hochstedler |
| 7,489,970 | B2 | 2/2009 | Lee et al. |
| 8,272,387 | B2 | 9/2012 | Essex et al. |
| 2001/0016711 | A1 | 8/2001 | Sorensen |
| 2002/0045887 | A1 | 4/2002 | DeHoogh et al. |
| 2002/0193676 | A1 | 12/2002 | Bodicker et al. |
| 2003/0202894 | A1 | 10/2003 | Leukanech |
| 2003/0204172 | A1 | 10/2003 | Steppe |
| 2003/0225363 | A1 | 12/2003 | Gordon |
| 2004/0002873 | A1 * | 1/2004 | Sachdeva ............ 705/2 |
| 2004/0024384 | A1 | 2/2004 | Novak |
| 2004/0074281 | A1 | 4/2004 | Lobdell et al. |
| 2004/0106915 | A1 | 6/2004 | Thoe |
| 2004/0253129 | A1 | 12/2004 | Sorensen |
| 2005/0041282 | A1 | 2/2005 | Rudolph et al. |
| 2005/0065462 | A1 | 3/2005 | Nazarifar |
| 2005/0113812 | A1 | 5/2005 | Viswanathan et al. |
| 2005/0186098 | A1 | 8/2005 | Davis |
| 2005/0234395 | A1 | 10/2005 | Mackool |
| 2005/0234441 | A1 | 10/2005 | Bisch |
| 2005/0285025 | A1 | 12/2005 | Boukhny et al. |
| 2005/0289173 | A1 * | 12/2005 | Vacca ............ 707/102 |
| 2006/0020915 | A1 | 1/2006 | Lloyd et al. |
| 2006/0114175 | A1 | 6/2006 | Boukhny |
| 2006/0235307 | A1 | 10/2006 | Boukhny et al. |
| 2006/0236242 | A1 | 10/2006 | Boukhny et al. |
| 2006/0248477 | A1 | 11/2006 | Boukhny et al. |
| 2008/0003555 | A1 | 1/2008 | Ekvall et al. |
| 2008/0004728 | A1 | 1/2008 | Essex et al. |
| 2008/0065243 | A1 | 3/2008 | Fallman et al. |
| 2008/0287922 | A1 | 11/2008 | Panduro |
| 2009/0048587 | A1 | 2/2009 | Avanzino et al. |
| 2009/0049397 | A1 | 2/2009 | Boukhny |
| 2009/0118714 | A1 | 5/2009 | Teodorescu |
| 2009/0171328 | A1 | 7/2009 | Horvath |
| 2009/0182266 | A1 | 7/2009 | Gordon et al. |

FOREIGN PATENT DOCUMENTS

| | | |
|---|---|---|
| JP | H11-053509 | 2/1999 |
| JP | 2000-56888 | 2/2000 |
| JP | 2000-515050 A | 11/2000 |
| JP | 2002-510980 | 4/2002 |
| JP | 2003-190181 | 7/2003 |
| JP | 2005-535395 A | 11/2005 |
| JP | 2006-271885 | 10/2006 |
| WO | 98/08448 | 3/1998 |
| WO | WO0232354 A1 | 4/2002 |
| WO | 2004/016182 A1 | 2/2004 |
| WO | 2004/091458 A1 | 10/2004 |
| WO | WO2005084570 A1 | 9/2005 |
| WO | WO 2006/060423 A1 | 6/2006 |
| WO | WO 2007/101154 A1 | 9/2007 |
| WO | WO 2009/023376 A2 | 2/2009 |
| WO | WO 2009/023376 A3 | 2/2009 |

OTHER PUBLICATIONS

International Searching Authority, Written Opinion of the International Searching Authority, International Application No. PCT/US2007/062810, Jul. 30, 2007, 6 pages.

http://www.nidek.ru/cv24000.shtml, downloaded Jun. 3, 2011, computer translation by http://translate.google.com/#, 7 pages.

http://goszakaz.perm.ru/, downloaded Aug. 1, 2011, computer translation by http://translate.google.com/#, 6 pages.

"Nidek CV-24000 New pages in ophthalmic surgery" in the journal "Eye," 2001, No. 3, pp. 27-28.

* cited by examiner

SYSTEM AND METHOD FOR A PROCEDURE BASED GRAPHICAL INTERFACE

CROSS REFERENCE TO RELATED APPLICATION

This application claims priority under 35 U.S.C. §119 to U.S. Provisional Patent Application No. 60/776,998 filed Feb. 27, 2006, the entire contents of which are incorporated herein by reference.

TECHNICAL FIELD OF THE INVENTION

The present invention relates to surgical procedures. More particularly, embodiments of the present invention relate to surgical procedures using ophthalmic surgical systems. Even more particularly, embodiments of the present invention relate to systems and methods for defining or conducting a surgical procedure using an ophthalmic surgical system.

BACKGROUND

The human eye can suffer a number of maladies causing mild deterioration to complete loss of vision. While contact lenses and eyeglasses can compensate for some ailments, ophthalmic surgery is required for others. Generally, ophthalmic surgery is classified into posterior segment procedures, such as vitreoretinal surgery, and anterior segment procedures, such as cataract surgery. More recently, combined anterior and posterior segment procedures have been developed.

The surgical instrumentation used for ophthalmic surgery can be specialized for anterior segment procedures or posterior segment procedures or support both. Such surgical instrumentation can comprise a Vitreoretinal and Cataract microsurgical console. Such a surgical console can provide a variety of functions depending on the surgical procedure and surgical instrumentation. For example, surgical consoles can expedite cataract surgeries (e.g. phacoemulsification procedures) by helping manage irrigation and aspiration flows into and out of a surgical site. And of course surgical consoles can provide other functions.

Thus, Vitreoretinal and Cataract microsurgical consoles usually have a defined set of functionality, such as vitreous cutting, vacuum, etc. Currently, interfaces to these surgical systems allow a user to interact with the surgical system based solely on the functionality of the system. Thus, if a user desires to implement one function he must select this function from a group of functions and configure the desired parameters for the use of the function. This method of interaction with a surgical console is highly inefficient. Many surgical procedures comprise many steps where each of the steps may encompass the use of one or more of the functions of the surgical console and different parameters or sub-modes for these functions. Furthermore, the number of steps and functionality of the surgical system utilized with each step may vary widely from procedure to procedure. Thus, when implementing a particular surgical procedure a user must remember the steps of that particular surgical procedure and for each of the steps select the appropriate function of the surgical console and configure the parameters for the function appropriately. This may require a large degree of interaction with the surgical console (e.g. use of a footswitch or other input methodology) in order to implement a surgical procedure. Therefore there is a need for a system and method for procedural based interaction with a surgical console.

SUMMARY OF THE INVENTION

Embodiments of the present invention provide systems and methods for defining and conducting surgical procedures which are substantially more convenient, more intuitive, nimbler and swifter than prior art systems and methods of procedure modification and creation. Embodiments of the present invention may allow each of the surgical steps of a surgical procedure to be defined and associated with a function of the surgical console using a GUI. The defined surgical procedure can then be saved and later invoked by a user of the surgical console to conduct the surgical procedure. When the saved surgical procedure is invoked representations of the defined surgical steps are displayed to the user using a GUI so the user can conduct the surgical procedure by navigating through the representations of the surgical steps such that when a representation of a surgical step is selected the surgical console is configured according to the functionality associated with that surgical step.

One embodiment of the present invention includes a method, computer readable medium or surgical system which allows for the definition of a surgical procedure which may be later invoked to conduct the surgical procedure. The method can comprise the steps of: providing a GUI on a surgical console, where the GUI allows a surgical procedure to be defined through the definition of one or more surgical steps and the surgical steps associated with functionality provided by the surgical console. The definition of the surgical procedure may then be saved and invoked at a subsequent time by a user to conduct the surgical procedure. When the surgical procedure is invoked a GUI is provided on the surgical console where the GUI comprises representations of the one or more surgical steps. When a representation of a surgical step is selected by a user the surgical console may be configured for the functionality associated with that surgical step. Thus, by proceeding through the representations of the one or more surgical steps presented to the user using the GUI a user may conduct the surgical procedure utilizing the functionality of the surgical console associated with each of the one or more surgical steps.

Embodiments of the present invention provide the advantage that a user may interact with a surgical consul according to a procedure based paradigm. By utilizing procedure based interaction only the surgical steps or functionality needed for a particular surgical procedure may be displayed to a user. Thus, the interface may be simpler and more intuitive, allowing navigation of the display to similarly become simpler (e.g. requiring fewer interactions with an input device such as a footswitch or the like) and allowing a surgical procedure to be more easily conducted. The ease of use of such an interface may also promote a user's ability to create, modify, customize or save various surgical procedures, which in turn, may lead to better sharing of various surgical procedures amongst colleagues or easier peer review of these surgical procedures.

BRIEF DESCRIPTION OF THE FIGURES

A more complete understanding of the present invention and the advantages thereof may be acquired by referring to the following description, taken in conjunction with the accompanying drawings in which like reference numbers indicate like features and wherein.

DETAILED DESCRIPTION

Preferred embodiments of the invention are illustrated in the FIGURES, like numerals being used to refer to like and corresponding parts of the various drawings.

Figure 1:
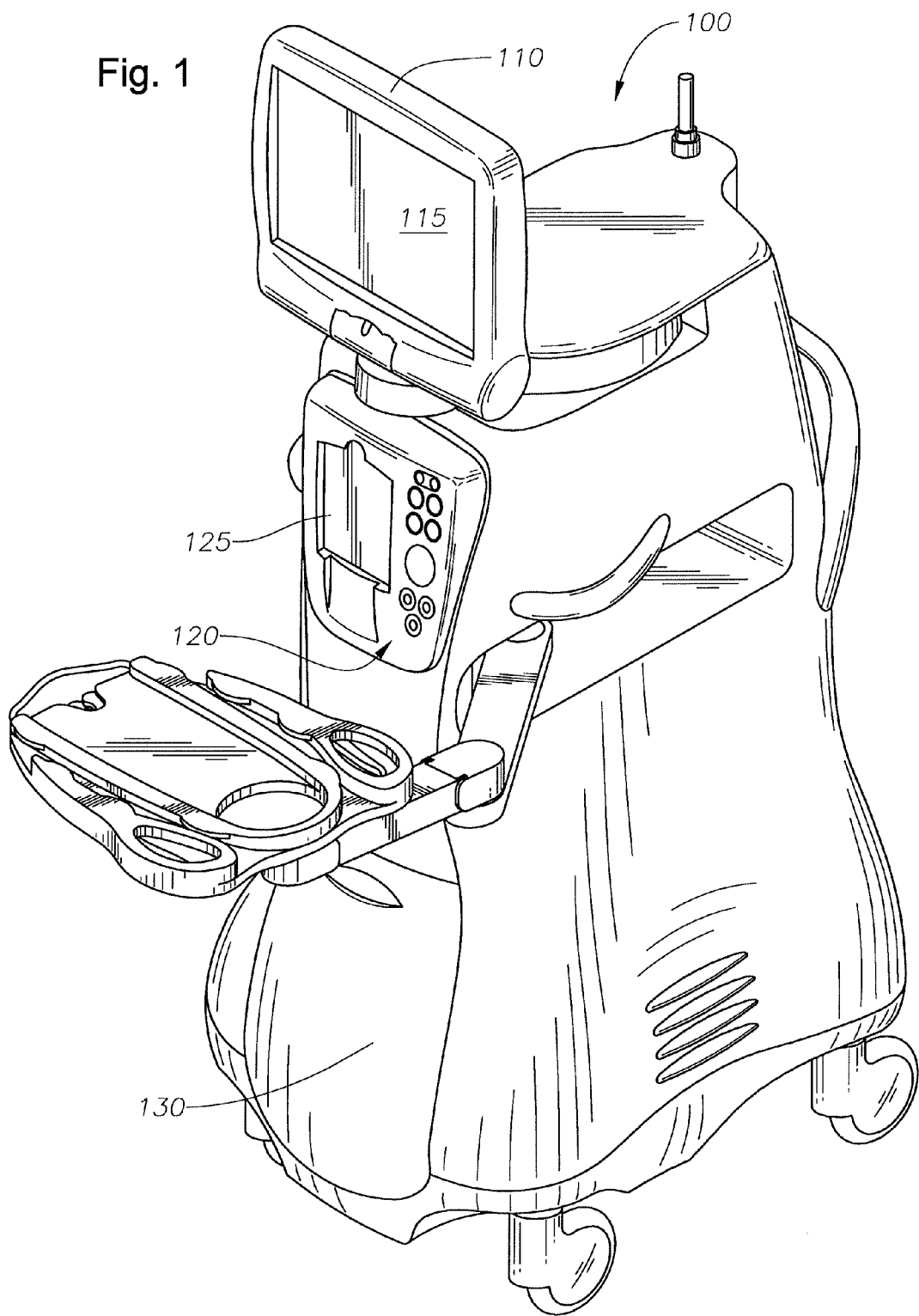
FIG. 1 is a diagrammatic representation of one embodiment of a surgical console.

Before elaborating on various embodiments of the present invention it may be helpful to illustrate surgical console with which embodiments of the present invention may be utilized. FIG. 1 is a diagrammatic representation of one embodiment of an ophthalmic surgical console 100. Surgical console 100 can include a swivel monitor 110 that has touch screen 115. Swivel monitor 110 can be positioned in a variety of orientations for whomever needs to see touch screen 115. Swivel monitor 110 can swing from side to side, as well as rotate and tilt. Touch screen 115 provides a GUI that allows a user to interact with console 100.

Surgical console 100 also includes a connection panel 120 used to connect various tools and consumables to surgical console 100. Connection panel 120 can include, for example, a coagulation connector, balanced salt solution receiver, connectors for various hand pieces and a fluid management system ("FMS") or cassette receiver 125. Surgical console 100 can also include a variety of user friendly features, such as a foot pedal control (e.g., stored behind panel 130) and other features.

Surgical console 100 is provided by way of example and embodiments of the present invention can be implemented with a variety of surgical systems. Example surgical systems in which various embodiments of the present invention can be used include, for example, the Series 2000® Legacy® cataract surgical system, the Accurus® 400VS surgical system, the Infiniti™ Vision System surgical system available from Alcon Laboratories Inc. of Fort Worth, Tex. Embodiments of the present invention can be implemented in other suitable surgical systems having a touch screen as would be understood by one of ordinary skill in the art.

In operation, a Graphical User Interface (GUI) may be displayed on screen 115, such that a user may interact with the surgical console 100. In one embodiment, the GUI for surgical system may allow a user to modally interact with surgical console 100. In other words, the GUI may present a user of surgical console 100 a set of icons or buttons corresponding to the entire range of functionality of surgical console 100 where the user can select from these function icons in order to utilize a particular functionality of surgical console 100. The user can then configure any parameters or sub-modes for the desired functionality and utilize this functionality. Thus, during a surgical procedure, for each step of the surgical procedure a user must manually interact with surgical console 100 to select the functionality desired for the step and configure any parameters or sub-modes for the step. As can be seen then, modal interaction with surgical console 100 may require a relatively large number of inputs (e.g. from foot pedal control or touch screen 115) to implement a surgical procedure and the GUI (or other method of interaction) with surgical console 100 may be quite cluttered and busy as it present the user with a wide variety of options corresponding to the entire range of functionality of surgical console 100.

Figure 2:
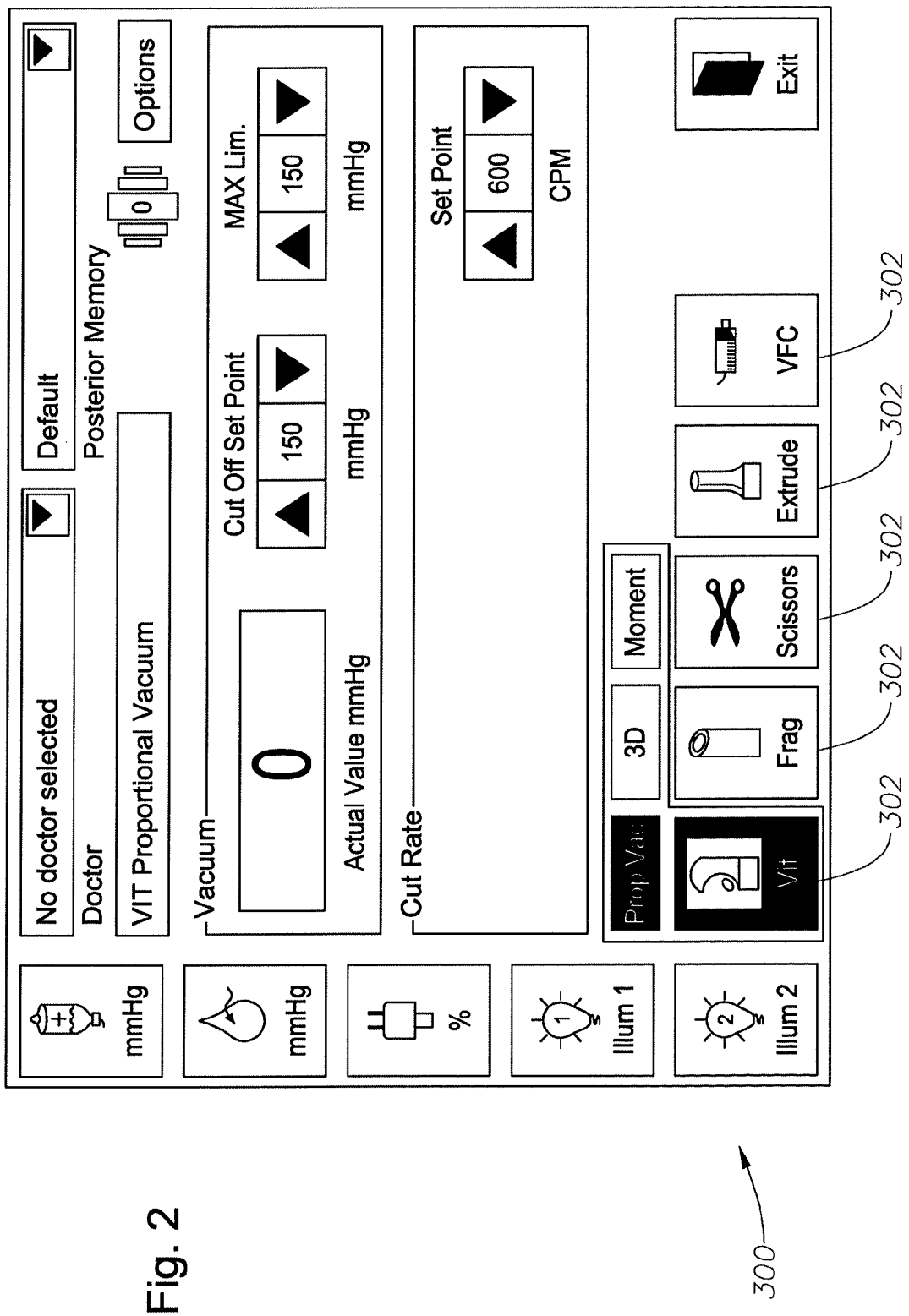
FIG. 2 is a representation of one embodiment of a graphical user interface (GUI)

For example, surgical console 100 may include functionality for vitreous cutting (Vit), vacuum (Extraction), Scissors, Viscous Fluid Control (VFC) and ultrasonic lens removal (Fragmatome). One embodiment of a GUI for modal based interaction with such a surgical console 100 is depicted in FIG. 2. Notice that GUI 300 presents icons 302 where each of icons 302 corresponds to one function of surgical console 100. Consequently, to utilize functionality represented by icons 302 a user of surgical console 100 may select the desired icon 302. To implement a surgical procedure then, for each step the icon 302 representing functionality desired for that step may be selected, and any parameters or sub-modes for that functionality configured. At every subsequent step of the surgical procedure where functionality of surgical console 100 is desired the user must again select the desired functionality corresponding to the step from icons 202 and configure any parameters or sub-modes. As may be imagined this is an inefficient method of interacting with surgical console, as extraneous interactions are needed to select and utilize desired functionality.

What is desired then is a clinically friendly method of interacting with a surgical console. To that end, attention is now directed to systems and methods for procedural based interaction with surgical consoles. Embodiments of the present invention may allow the definition of a surgical procedure, which utilizes the functionality of a surgical console, the surgical console can then display a representation of the surgical procedure comprising representations of the surgical steps of the surgical procedure such that a user can implement the surgical procedure using the surgical console by navigating through the displayed representations. More particularly, in one embodiment, each of the surgical steps of a surgical procedure may be defined and associated with a function of the surgical console. The defined surgical procedure can then be saved to a database and later invoked by a user of the surgical console to conduct the surgical procedure. When the saved surgical procedure is invoked representations of the defined surgical steps are displayed to the user so the user can conduct the surgical procedure by navigating through the representations of the surgical steps such that when a representation of a surgical step is selected the surgical console is configured according to the functionality associated with that surgical step.

More specifically, embodiments of the present invention may use touch screen 115 to present an interactive graphical user interface ("GUI") to the user. Specifically, the user can use the interactive GUI to define a surgical procedure (e.g. a posterior surgical procedure or the like. The defined surgical procedure may later be invoked to implement the surgical procedure. When this surgical procedure is invoked an interactive GUI on touch screen 115 displays representations of the steps of the surgical procedure to a user such that the user may conduct the surgical procedure using associated functionality of the surgical console by navigating through the representation of the steps of the surgical procedure presented to the user, for example by using touch screen 115, a foot pedal control or the like. By utilizing a procedure based interface such as this fewer interactions with the surgical consol (e.g. inputs using touch screen 115 or a foot pedal control) may be used during the implementation a surgical procedure.

By allowing a user to define a surgical procedure in this manner a whole variety of advantages may be realized. First, only the steps needed to perform a particular surgical procedure may be displayed to a user, and these steps may be given intuitive or mnemonic names which represent or define the surgical step. Furthermore, as only the required steps for the surgical procedure are displayed, where these step may defined to invoke specific functionality of the surgical console, the amount of interaction with a surgical console required to perform a certain surgical procedure may be greatly reduced. As an added benefit, by allowing a user to modify, customize or save surgical procedures (for example according to the procedure depicted in U.S. patent application Ser. No. 11/479,668, "System and Method For the Modification of Surgical Procedures Using a Graphical Drag and Drop Interface," filed on Jun. 30, 2006, which is hereby fully incorporated herein by reference for all purposes), a particular user's approach to a surgical procedure may be saved and compared with other users definition of a particular surgical procedure, or provided to another user for their use.

Figure 3:
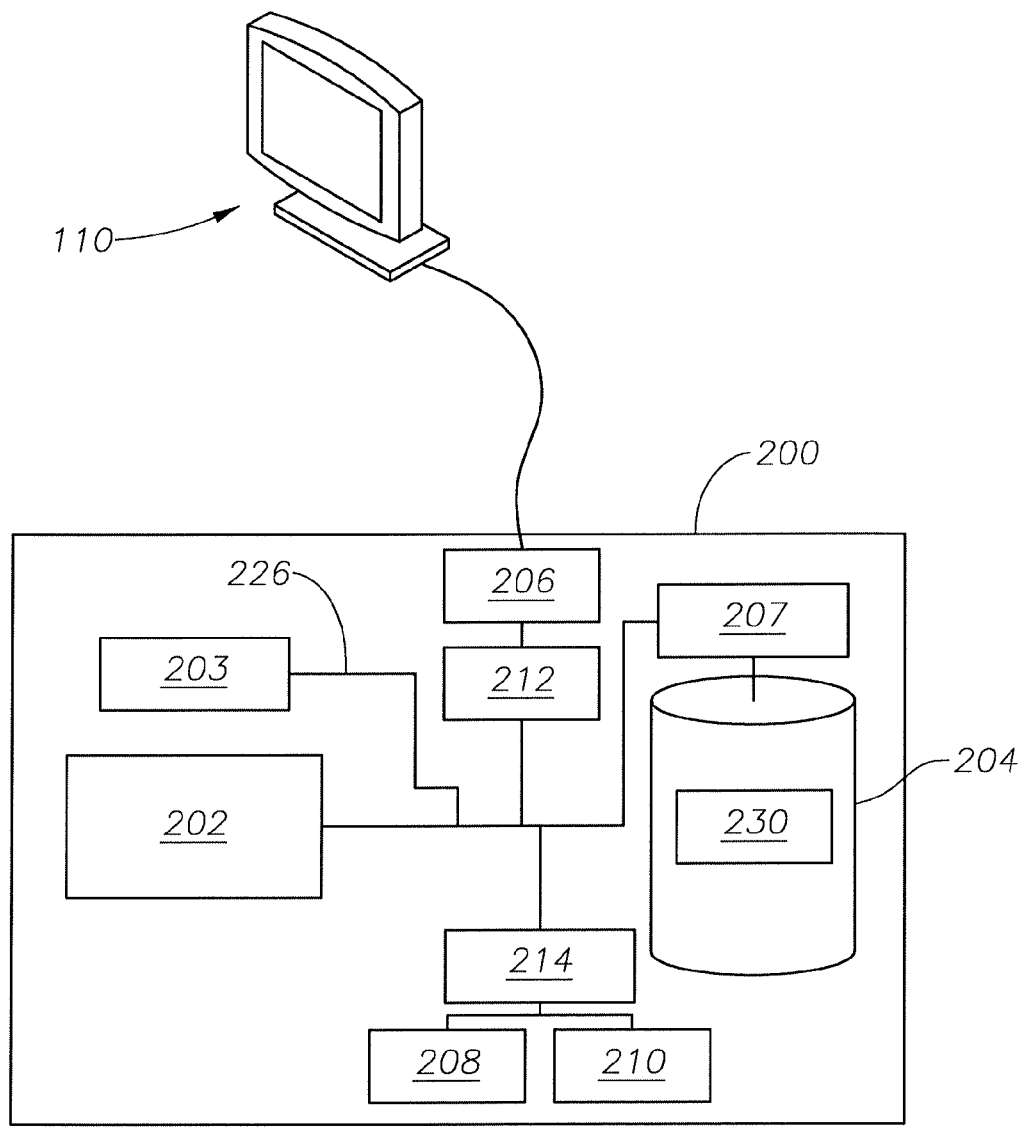
FIG. 3 is a diagrammatic representation of one embodiment of a controller for surgical instrumentation.

It may be useful at this point to briefly describe portions of surgical console 100 which may be used in implementing embodiments of the present invention. FIG. 3 is a diagrammatic representation of a surgical instrumentation controller 200 ("controller 200"). Controller 200 can be onboard or connected to surgical instrumentation such as surgical console 100. Controller can include a processor 202, such as an Intel Pentium 4 based processor (Intel and Pentium are trademarks of Intel Corporation of Santa Clara, Calif.), a primary memory 203 (e.g., RAM, ROM, Flash Memory, EEPROM or other computer readable medium known in the art) and a secondary memory 204 (e.g., a hard drive, disk drive, optical drive or other computer readable medium known in the art). A memory controller 207 can control access to secondary memory 204. Controller 200 can include I/O interfaces, such as touch screen interface 206. A video controller 212 can control interactions over the touch screen interface 206. Similarly, an I/O controller 214 can control interactions over I/O interfaces 208 and 210. Controller 200 can include a variety of input devices. Various components of controller 200 can be connected by a bus 226.

Secondary memory 204 can store a variety of computer instructions that include, for example, an operating system such as a Windows operating system (Windows is a trademark of Redmond, Wash. based Microsoft Corporation) and applications that run on the operating system, along with a variety of data. More particularly, secondary memory 204 can store a software program 230 that controls the procedural flow of a surgery based on a procedural paradigm. During execution by processor 202, portions of program 230 can be stored in secondary memory 204 and/or primary memory 203.

In operation, program 230 can be executable by processor 202 to provide a GUI to the user (e.g., through monitor 110) that shows a first display which represents allows a definition of a surgical procedure. This surgical procedure may be defined by the definition of an ordered set of steps of the surgical procedure and the association of functionality of surgical console 100 with the defined steps. The defined surgical procedure may then be saved (for example to primary memory 203 or secondary memory 204) for later invocation by a user. When such a surgical procedure is invoked by a user program 230 may provide a GUI to the user displaying representations of each of the set of defined steps such that when a user selects one of the representations of the defined steps surgical console 100 is configured according to the definition of that step (e.g. surgical console 100 is configured to perform the functionality associated with that step, including any parameters or sub-modes defined in conjunction with that step). Thus, by navigation through the displayed representations of steps of the surgical procedure, the surgical procedure may be conducted using the associated functionality of the surgical console corresponding to each of the steps.

Controller 200 of FIG. 3 is provided by way of example only and it should be understood that embodiments of the present invention can implemented as a set of computer instructions stored on a computer readable medium in a variety of computing devices. Program 230 can be executable to receive and store data over a network and can include instructions that are stored at a number of different locations and are executed in a distributed manner. While shown as a stand alone program in FIG. 3, it should be noted that program 230 can be a module of a larger program, can comprise separate programs operable to communicate data to each other or can be implemented according to any suitable programming architecture or language.

Figure 4:
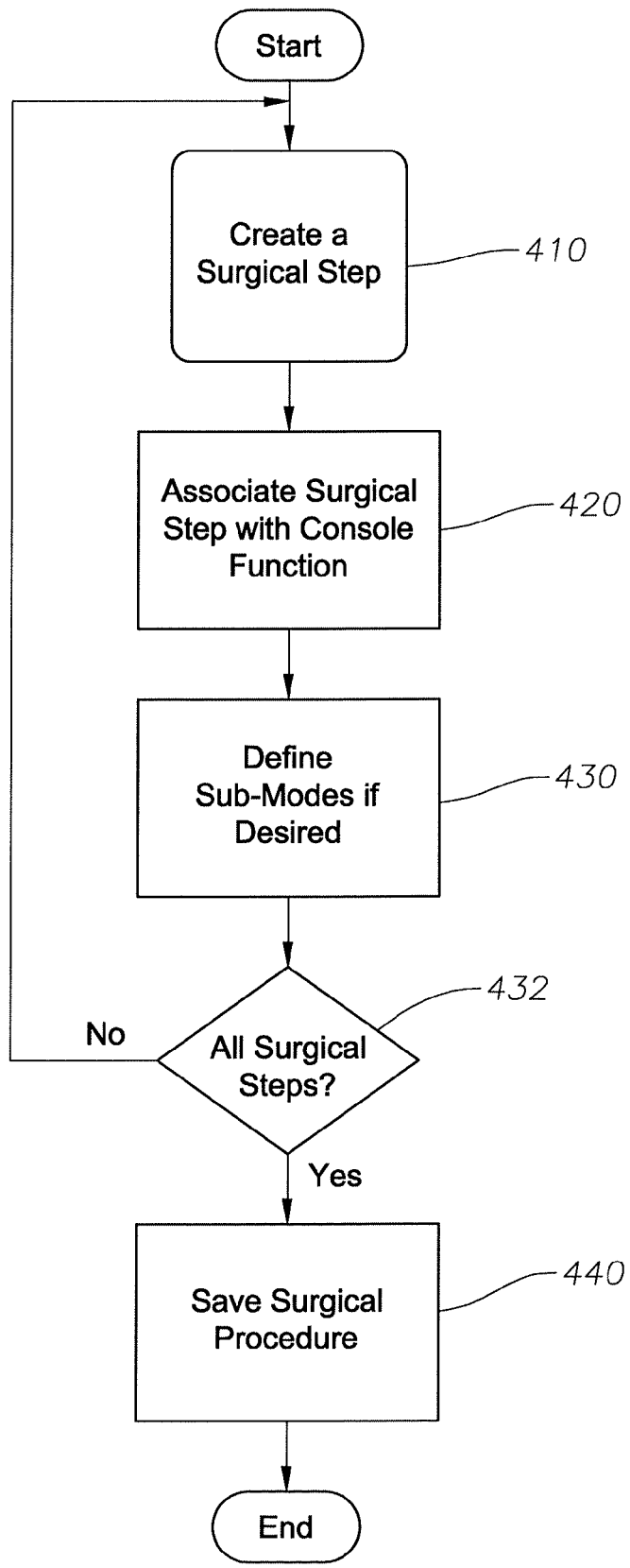
FIG. 4 is a flow diagram illustrating one embodiment of a method for defining a surgical procedure.

Moving now to FIG. 4, a flow diagram for one embodiment of method for defining a surgical procedure is depicted. At step 410 a user of surgical console may create a surgical step for surgical procedure. The creation of the surgical step may comprise labeling the surgical step with the surgical task to be accomplished, a surgically significant name (e.g. surgical task to be accomplished), or any other another type of mnemonic for the surgical step. After a surgical step for a surgical procedure is created it may be associated with a particular function of the surgical console 100 at step 420, such that when the surgical step is selected by a user surgical console may be configured or made operable to perform this function. Any particular parameters or sub-modes which it may be desired to define in conjunction with the surgical step (e.g. associated with the function corresponding to the surgical step) can then be defined at step 430 so that surgical console 100 may additionally be configured or made operable according to these parameters or sub-modes when the surgical step is invoked by a user. For each of the surgical steps of a surgical procedure, then, the process of creating at step 410, associating with a particular function at step 420 and defining parameters or sub-modules may be repeated until each of the surgical steps of the surgical process is completely defined (as determined at step 432). At that point, the defined surgical procedure may be saved utilizing a descriptive or otherwise appropriate name at step 440.

Figure 5:
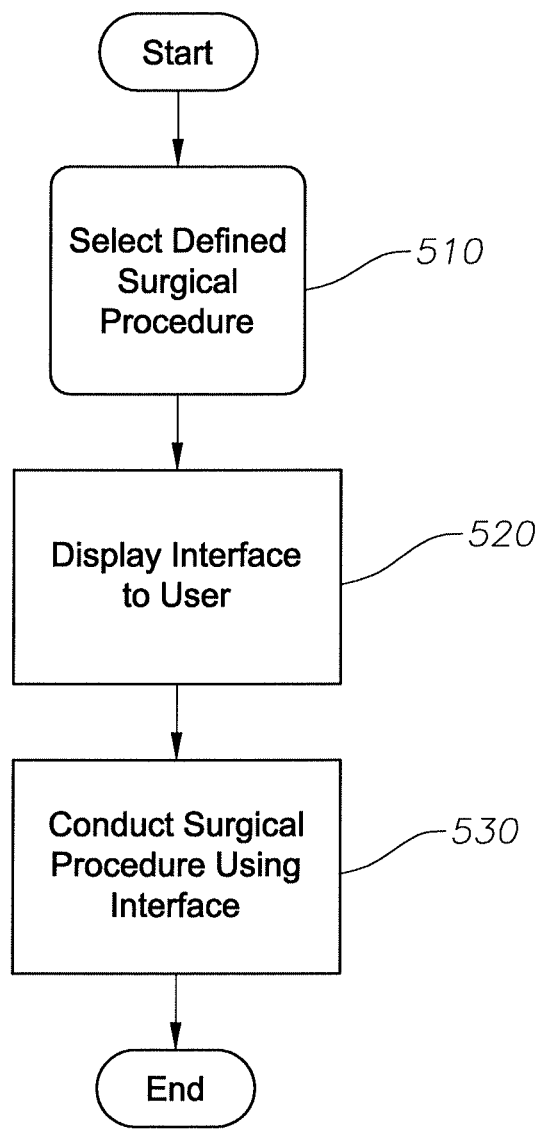
FIG. 5 is a flow diagram illustrating one embodiment of a method for invoking a surgical procedure.

Turning now to FIG. 5, a flow diagram for one embodiment of the use of a defined surgical procedure is depicted. A defined surgical procedure may be selected at step 510. This surgical procedure may, for example, be selected from a set of defined surgical procedures on surgical console 100 which may have been defined or saved by a user or provided by the manufacturer of surgical console 100. When a particular defined surgical procedure is selected at step 510, then, an interface for this surgical procedure may be displayed to a user at step 520 and using this interface a user may conduct the surgical procedure at step 530. This interface may comprise, in one embodiment, a GUI which presents a representation of each of the defined surgical steps of the surgical procedure. A user of the GUI may navigate through the representation of each of the surgical steps using an input method of surgical console 100 to implement the surgical procedure. More specifically, when a representation of a surgical step of the surgical procedure is selected by a user, surgical console 100 may be configured according to the functionality (and any associated parameters or sub-modes defined for the surgical step) such that the surgical step may be performed by the user using the associated functionality of surgical console 100.

Figure 6:
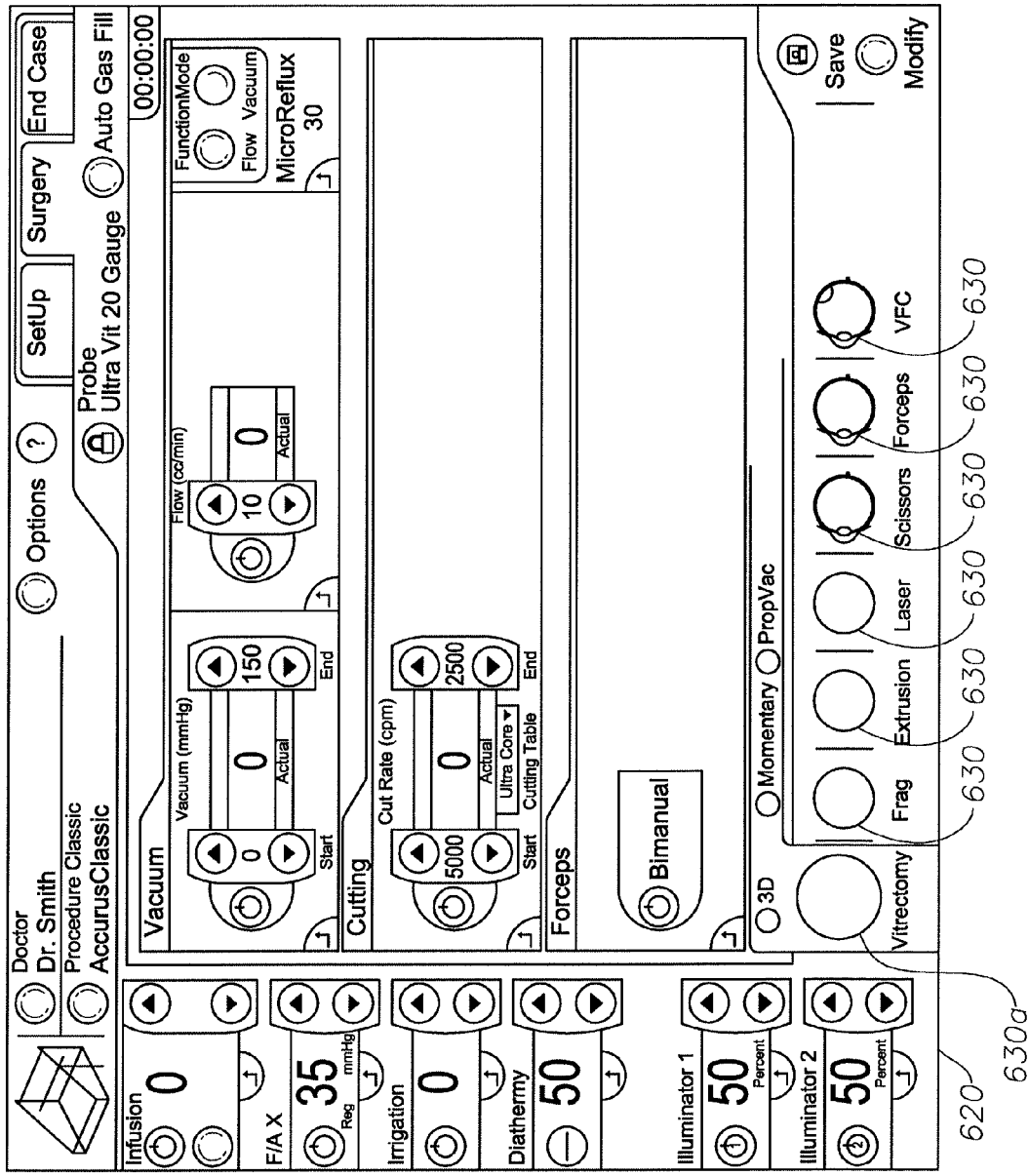
FIGS. 6-10 are representations of one embodiment of a GUI.

It may be useful here to give an example of an embodiment of such interfaces. FIG. 6 shows an embodiment of a GUI 610 which might be displayed on a surgical console touch screen (e.g. touch screen 115). As shown in FIG. 6, GUI 610 comprises a portion that displays a representation of a surgical procedure. For example, GUI 610 can comprise a surgical procedural display 620 which displays representations 630 of the surgical steps for a surgical procedure named "Accurus-Classic" as displayed in procedure name portion 642 of GUI 610. Thus, by navigating through the representations 630 of the surgical steps of the surgical procedure a user may implement the surgical procedure using the functionality of a surgical console, as described above. Note that here a user has selected representation 630*a* of a surgical step named "Vitrectomy", thus the surgical console is configured for functionality associated with that surgical step and GUI 610 displays the current configuration of the surgical console for that surgical step, including any sub-modes (e.g. "3D") or any other configured parameters. It will be realized that GUI 610 is but one example of the organization of an interface for the use of a defined surgical procedure and that a surgical procedure of surgical steps can be manifested in any number of ways and combinations, including appearing together on the same touch screen or on different screens or any conceivable combination thereof.

Figure 7:
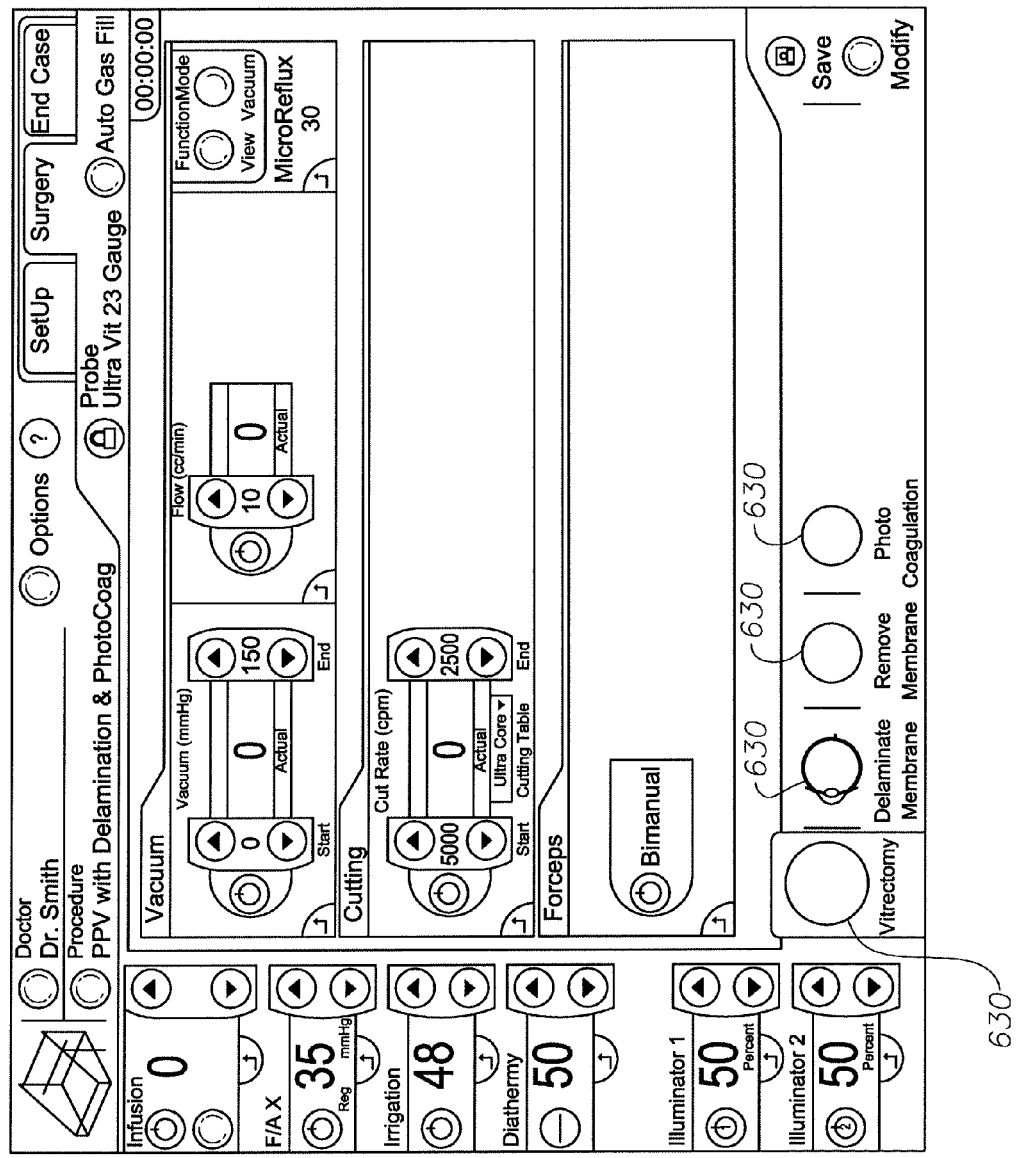
Figure 8:
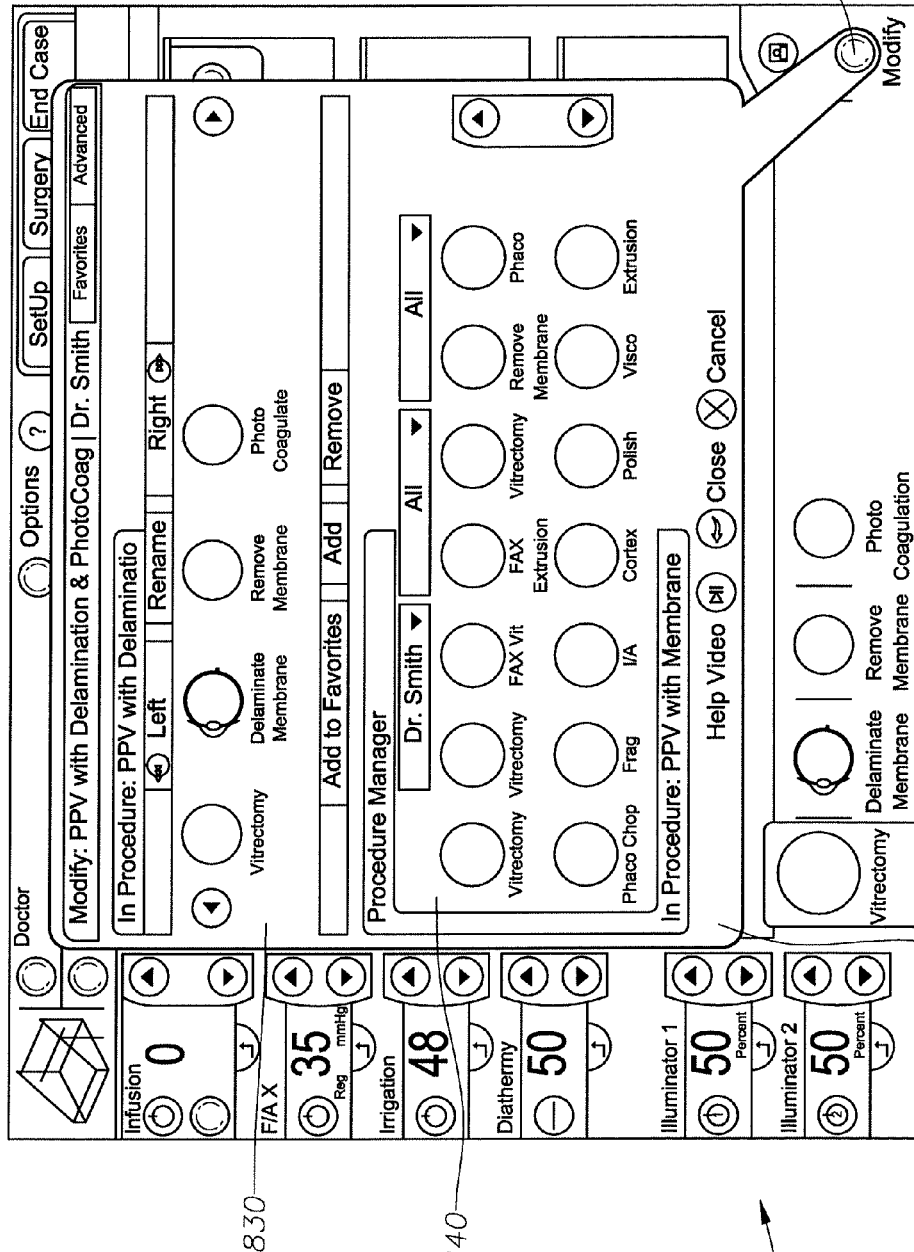
Figure 9:
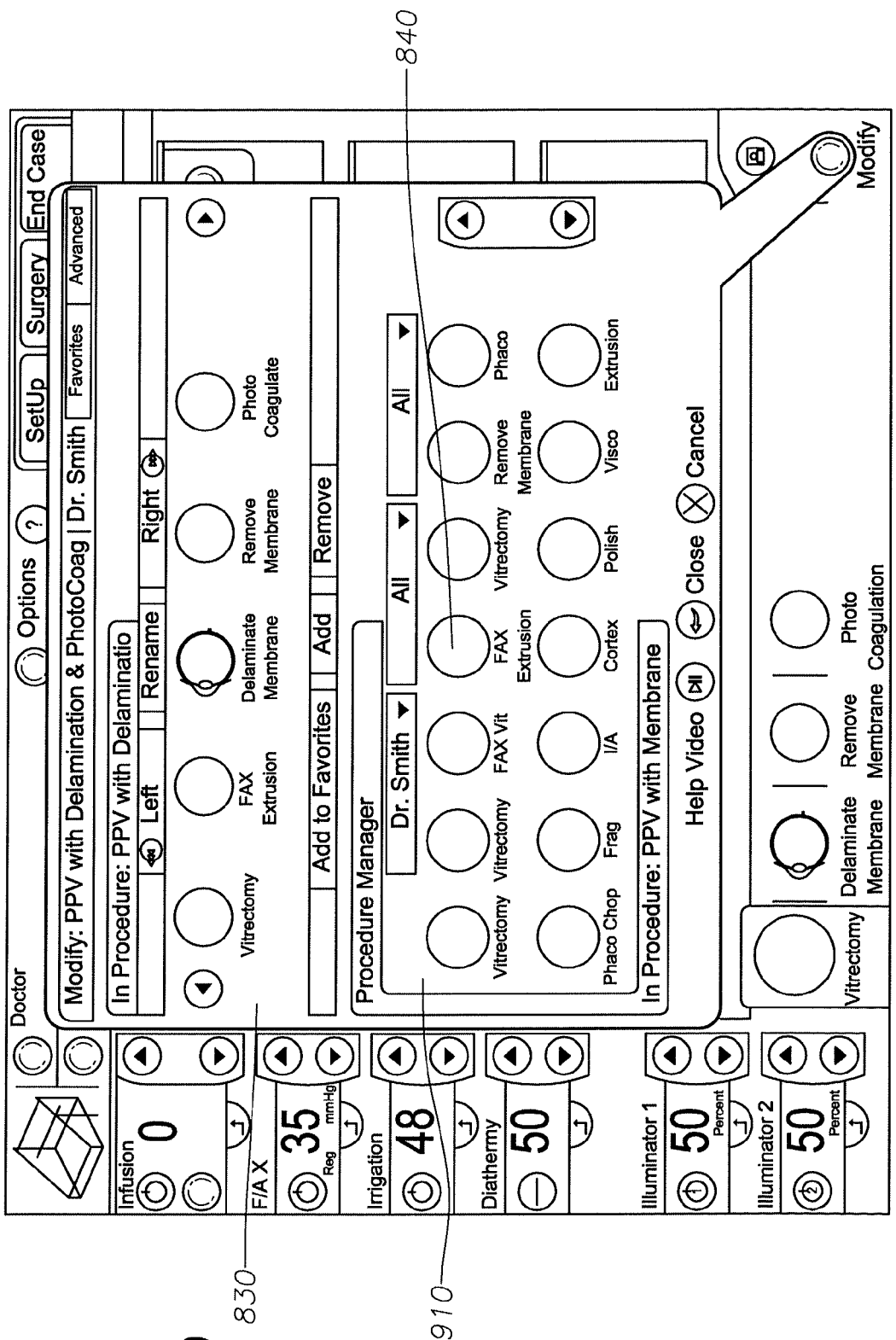
Figure 10:
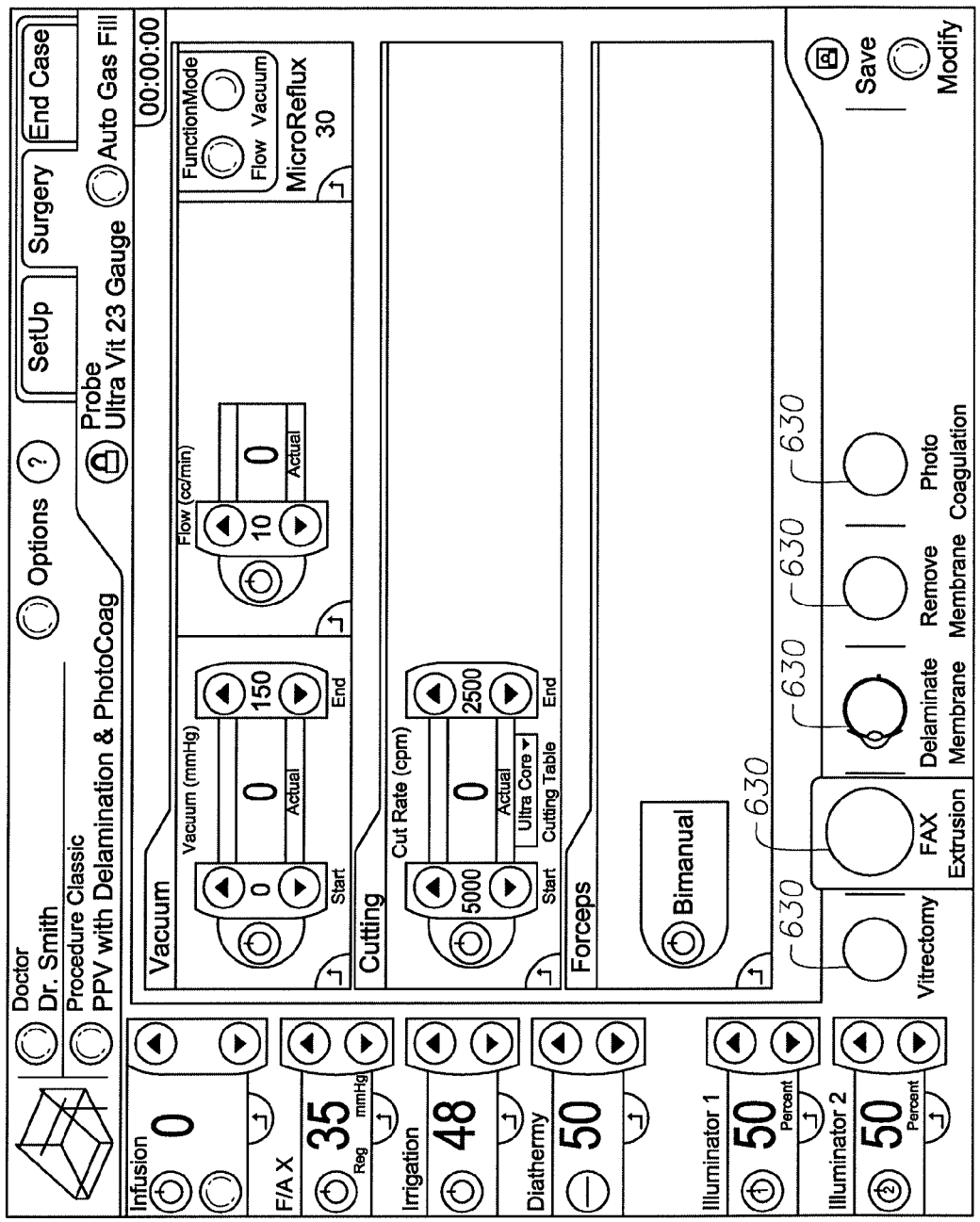

Moving to FIGS. 7-10, one embodiment of the modification of a surgical procedure is depicted. FIG. 7 depicts one embodiment of GUI 610 displaying a surgical procedure named "PPV with Delamination & PhotoCoag" which has representations 630 of four surgical steps: "Vitrectomy", "Delaminate Membrane", "Remove Membrane" and "Photo Coagulation". In FIG. 8 a user has selected to modify the surgical procedure "PPV with Delamination & PhotoCoag" by pressing the modify button 810, such that GUI 610 now shows a modify screen 820 with two sections: section 830 displaying representations of the current surgical steps comprising the surgical procedure "PPV with Delamination & PhotoCoag" and section 840 which displays representations of a set of surgical steps which may be added to the set of steps comprising the surgical procedure. Moving now to FIG. 9 a user has selected representation 910 of surgical step "FAX Extrusion" from section 840 of GUI 610 and chosen to add this surgical step to the surgical steps comprising the surgical procedure "PPV with Delamination & PhotoCoag". The added step surgical step "FAX Extrusion" now appears in section 830 which includes the current surgical steps comprising the surgical procedure. Thus, as depicted in FIG. 10, after a user completes the modification of the surgical procedure "PPV with Delamination & PhotoCoag" the representations 630 of the surgical steps comprising this surgical procedure now includes a representation of the surgical step of "FAX Extrusion", and a user may implement this step during the surgical procedure by selecting the representation for this surgical step.

Although the present invention has been described in detail herein with reference to the illustrated embodiments, it should be understood that the description is by way of example only and is not to be construed in a limiting sense. It is to be further understood, therefore, that numerous changes in the details of the embodiment of this invention and additional embodiments of this invention will be apparent, and may be made by, persons of ordinary skill in the art having reference to this description. It is contemplated that all such changes and additional embodiments are within scope of the invention as claimed below.

What is claimed is:

1. A method for conducting a surgical procedure, comprising:
   receiving, for a first surgical step, a user-associated functionality and at least one defined parameter;
   providing a Graphical User Interface (GUI) for a surgical console, wherein the GUI comprises a representation of each of one or more surgical steps of the surgical procedure, each of the surgical steps corresponding to a function of the surgical console;
   detecting that a representation of the first surgical step of the one or more surgical steps has been selected; and
   configuring the surgical console according to the user-associated function and at least one defined parameter corresponding to the first surgical step;
   detecting that a representation of a second surgical step of the one or more surgical steps has been selected; and
   configuring the surgical console according to the function corresponding to the second surgical step;
   wherein a user is enabled to navigate through the GUI and interact with the surgical console so as to cause the console to be set up to conduct a multiple step surgical procedure.

2. The method of claim 1, further comprising configuring the surgical console according to a sub-mode defined for the first surgical step.

3. The method of claim 1, wherein each of the representations has a corresponding label.

4. The method of claim 1, further comprising defining the surgical procedure, where defining the surgical procedure comprises:
   creating the one or more surgical steps, wherein creating each of the surgical steps comprises labeling the surgical step; and
   associating the corresponding function of the surgical console with each of the surgical steps.

5. The method of claim 1, wherein providing the GUI consists of providing only the surgical steps of a selected surgical procedure.

6. The method of claim 5, further comprising:
   receiving a user indication to modify the surgical procedure;
   upon receiving the user indication to modify the surgical procedure, presenting the user with additional representations of surgical steps to add to the surgical procedure;
   receiving an indication from the user of a representation of a surgical step to add to the surgical procedure; and
   adding the representation of the surgical step to the surgical procedure such that when only the surgical steps of the selected surgical procedure are displayed, the added surgical step is included in the displayed surgical steps.

7. The method of claim 1, further comprising:
   associating each of the one or more surgical steps with a corresponding function of the surgical console;
   defining at least one particular parameter for at least one of the one or more surgical steps;
   storing the at least one particular parameter in association with the surgical procedure such that when the surgical procedure is invoked, the at least one particular parameter is used in the surgical procedure.

8. The method of claim 1, further comprising:
   associating each of the one or more surgical steps with a corresponding function of the surgical console;
   defining at least one sub-mode for at least one of the one or more surgical steps;
   storing the at least one sub-mode in association with the surgical procedure such that when the surgical procedure is invoked, the at least one sub-mode is used in the surgical procedure.

9. A computer readable medium comprising a set of computer instructions, comprising instructions executable by a processor for:
   receiving, for a first surgical step, a user-associated functionality and at least one defined parameter;

providing a Graphical User Interface (GUI) for a surgical console, wherein the GUI comprises a representation of each of one or more surgical steps of the surgical procedure, each of the surgical steps corresponding to a function of the surgical console;

detecting that a representation of the first surgical step of the one or more surgical steps has been selected; and configuring the surgical console according to the user-associated function and at least one defined parameter corresponding to the first surgical step;

detecting that a representation of a second surgical step of the one or more surgical steps has been selected; and configuring the surgical console according to the function corresponding to the second surgical step;

wherein a user is enabled to navigate through the GUI and interact with the surgical console so as to cause the console to be set up to conduct a multiple step surgical procedure.

10. The computer readable medium of claim 9, wherein the instructions are executable for configuring the surgical console according to a sub-mode defined for the first surgical step.

11. The computer readable medium of claim 9, wherein each of the representations has a corresponding label.

12. The computer readable medium of claim 9, wherein the instructions are executable for defining the surgical procedure, where defining the surgical procedure comprises:

creating the one or more surgical steps, wherein creating each of the surgical steps comprises labeling the surgical step; and associating the corresponding function of the surgical console with each of the surgical steps.

13. The computer readable medium of claim 9, wherein the set of computer instructions are further executable by a processor for:

associating each of the one or more surgical steps with a corresponding function of the surgical console;

defining at least one particular parameter for at least one of the one or more surgical steps;

storing the at least one particular parameter in association with the surgical procedure such that when the surgical procedure is invoked, the at least one particular parameter is used in the surgical procedure.

14. The computer readable medium of claim 9, wherein the set of computer instructions are further executable by a processor for:

associating each of the one or more surgical steps with a corresponding function of the surgical console;

defining at least one sub-mode for at least one of the one or more surgical steps;

storing the at least one sub-mode in association with the surgical procedure such that when the surgical procedure is invoked, the at least one sub-mode is used in the surgical procedure.

15. A surgical system comprising:
a display;
a surgical console; and
a controller coupled to the display and the surgical console, the controller configured for:

receiving, for a first surgical step, a user-associated functionality and at least one defined parameter;

providing a Graphical User Interface (GUI) for the surgical console, wherein the GUI comprises a representation of each of one or more surgical steps of the surgical procedure, each of the surgical steps corresponding to a function of the surgical console;

detecting that a representation of the first surgical step of the one or more surgical steps has been selected; and configuring the surgical console according to the user-associated function and at least one defined parameter corresponding to the first surgical step;

detecting that a representation of a second surgical step of the one or more surgical steps has been selected; and configuring the surgical console according to the function corresponding to the second surgical step;

wherein a user is enabled to navigate through the GUI and interact with the surgical console so as to cause the console to be set up to conduct a multiple step surgical procedure.

16. The surgical system of claim 15, wherein the controller is further configured for configuring the surgical console according to a sub-mode defined for the first surgical step.

17. The surgical system of claim 15, wherein each of the representations has a corresponding label.

18. The surgical system of claim 15, wherein the controller is further configured for allowing the surgical procedure to be defined, where defining the surgical procedure comprises:

creating the one or more surgical steps, wherein creating each of the surgical steps comprises labeling the surgical step; and associating the corresponding function of the surgical console with each of the surgical steps.

19. The surgical system of claim 15, wherein the controller is further configured for:

associating each of the one or more surgical steps with a corresponding function of the surgical console;

defining at least one particular parameter for at least one of the one or more surgical steps;

storing the at least one particular parameter in association with the surgical procedure such that when the surgical procedure is invoked, the at least one particular parameter is used in the surgical procedure.

20. The surgical system of claim 15, wherein the controller is further configured for:

associating each of the one or more surgical steps with a corresponding function of the surgical console;

defining at least one sub-mode for at least one of the one or more surgical steps;

storing the at least one sub-mode in association with the surgical procedure such that when the surgical procedure is invoked, the at least one sub-mode is used in the surgical procedure.

* * * * *